United States Patent [19]

Washer

[11] Patent Number: 4,592,677

[45] Date of Patent: Jun. 3, 1986

[54] DESICCANT BED ON HYDROCARBON CHARGED TO AND REMOVED FROM UNDERGROUND (SALT) CAVERN

[75] Inventor: Stone P. Washer, Bartlesville, Okla.

[73] Assignee: Phillips Petroleum Company, Bartlesville, Okla.

[21] Appl. No.: 591,754

[22] Filed: Mar. 21, 1984

[51] Int. Cl.⁴ .............................................. B65G 65/30
[52] U.S. Cl. ..................................... 405/59; 210/677; 210/689; 405/53
[58] Field of Search .............................. 405/58, 52–55; 210/689, 677, DIG. 6

[56] References Cited

U.S. PATENT DOCUMENTS 2,626,675  1/1953  Maher ........................... 210/DIG. 6
4,029,580  6/1977  Lange ........................... 210/DIG. 6

Primary Examiner—Dennis L. Taylor
Attorney, Agent, or Firm—E. T. Kittleman

[57] ABSTRACT

Hydrocarbon liquid, such as propylene, is charged (dry) from manufacture by way of a bed of desiccant into a salt (brine-containing) cavern for wet storage, thusly regenerating the wet desiccant having been used to dry wet hydrocarbon yielded from the cavern as product.

15 Claims, 1 Drawing Figure

DESICCANT BED ON HYDROCARBON CHARGED TO AND REMOVED FROM UNDERGROUND (SALT) CAVERN

FIELD OF THE INVENTION

The invention pertains to methods for storage of hydrocarbons in salt caverns. In one aspect, the invention pertains to methods to provide a relatively dry hydrocarbon from wet storage over brine to use purposes. In a further aspect, the invention pertains to underground storage caverns in which a hydrocarbon fluid being stored displaces brine upon being received into the cavern, and in turn is displaced by brine upon removing the hydrocarbon fluid from the storage cavern. In another aspect, the invention pertains to a cavern with drying apparatus.

BACKGROUND OF THE INVENTION

Expanding production and uses of hydrocarbon fluids both as fuel gases and as raw materials for various purposes create a definite problem in providing large storage facilities for these fluids. Sometimes long storage of some hydrocarbons, such as propylene, is required to provide capacity for variable demands.

Salt storage caverns have provided a convenient answer, easily handling the frequently several hundred pound per square inch storage pressures required, and providing relatively economical large storage capacities to provide response to seasonal peak load demands and requirements, and corresponding storage during seasonal slack periods.

In a cavern formed in a salt strata, a pool of brine generally occupies the lower portion of the cavern volume, and the stored hydrocarbon fluid occupies the upper portion. Thus, the cavern always is maintained full. An access bore is provided, relatively small in diameter, with dual fluid passages so that fluid handling means at the surface provide capability for brine to be pumped in or out of the lower area of the cavern, and hydrocarbon fluid then can be taken from the upper area. Hydrocarbon product is added to storage by pumping into the cavern under sufficient pressure to displace brine therein back to the surface. Displaced brine is maintained at ground level in a brine pit or reservoir, and then is returned to the salt cavern to replenish the brine volume as hydrocarbon fluid is retrieved. Precautions are taken to assure that the brine in and out is always salt-saturated to avoid enlarging the brine cavern and/or to avoid salt dropout at the surface due to changes in temperature.

However, with a "wet" stored hydrocarbon, other problems exist. The hydrocarbons from pipeline or production for storage normally is dry. It becomes wet in the cavern. Upon retrieval, it must be re-dried. Moisture in transmission pipelines is undesirable. Re-drying is a relatively expensive procedure requiring desiccant beds to dry the retrieved wet hydrocarbon, periodic regeneration with hot gases which is an energy-consuming step, and so on. However, this is and has been the current practice.

Needed is a method and apparatus to wet store hydrocarbon fluids, and yet retrieve the hydrocarbon fluids relatively dry, in an energy efficient manner.

BRIEF DESCRIPTION OF THE INVENTION

I have discovered a method of and an apparatus for introducing wet hydrocarbon to storage, and retrieving dry hydrocarbon from storage, essentially energy free. If further drying is required, this can be handled by the hot gas generating driers in conventional manner, but the operation of such becomes much simpler and cheaper.

According to my method and apparatus, a desiccant drier bed is installed such that all hydrocarbon product flows through the dessicant drier bed whether entering or leaving the cavern storage. The normally dry hydrocarbon product directed to storage passes through the dessicant bed, thus in effect regenerating the bed and carrying moisture back to the cavern, which helps maintain appropriate moisture relationship in the cavern. Thus the entering dry product retrieves and carries with it moisture from the desiccant bed which has been previously removed and retained by the bed from previously stored removed hydrocarbon product. Upon retrieval of the now wet hydrocarbon fluid, from storage, the wet hydrocarbon then passes back through the desiccant bed in reverse flow, and therein becomes substantially dry before taken to normal usage. If further drying is necessary by the usual energy-intensive methods, then the requirements of such in the way of regeneration heat become much reduced due to much reduced frequency of conventional regeneration procedures.

It is an object of my invention to provide dry retrieval of wet stored hydrocarbons, in an energy efficient method using an energy efficient apparatus.

BRIEF DESCRIPTION OF THE DRAWING

A cavern 1 is shown in irregular outline within a salt strata 2 positioned above bed rock 3 and below surface strata 4. Contained in the salt cavern 1 is a lower layer or volume of aqueous brine 5, and above the brine is a layer or volume of hydrocarbon fluid 6, which can be liquid or gas, fitting the remaining volume of cavern 1. Preforating the surface of the ground 7 and connecting with cavern 1 is a stringer assembly 8 comprising connecting piping 9 for hydrocarbon input and removal and providing connection to and fluid access with the upper volume 6 of the cavern; and a brine input-output tubing 11 which then connects with and provides fluid access with the lower or brine volume 5 of the cavern. As hydrocarbon fluid flows or is pumped in 12 to storage 6, brine 5 is removed out of storage via 11, 13 to surface storage 14. As hydrocrbon fluid 6 is drawn out 15 from storage, brine 14 then is added back 16, 11 to lower volume 5 of the cavern. The interface 16' between the lower brine 5 and the hydrocarbon fluid 6 raises or lowers as hydrocarbon 15 is withdrawn 15 or added back 12 to cavern storage.

In accordance with my invention, at least one drier, shown in the drawing as here a pair of driers 21 and 21a, is added to the hydrocarbon fluid line 22. The hydrocarbon fluid received 22 flows 23, 23a through one or both driers 21 or 21a, and enters 24, 24a the hydrocarbon inlet line 25 in a moist condition for pumping 12 into hydrocarbon storage 6. Upon withdrawal 15 of hydrocarbon fluid 6 from storage, the hydrocarbon fluid being withdrawn flows through line 25 into 26 or 26a to the respective drier 21 or 21a, exits dry or substantially dry 27 or 27a for return 28 for transport to such usages as may be required as fuel, chemical conversion, polymerization, or the like, depending on the hydrocarbon involved.

Figure 1:
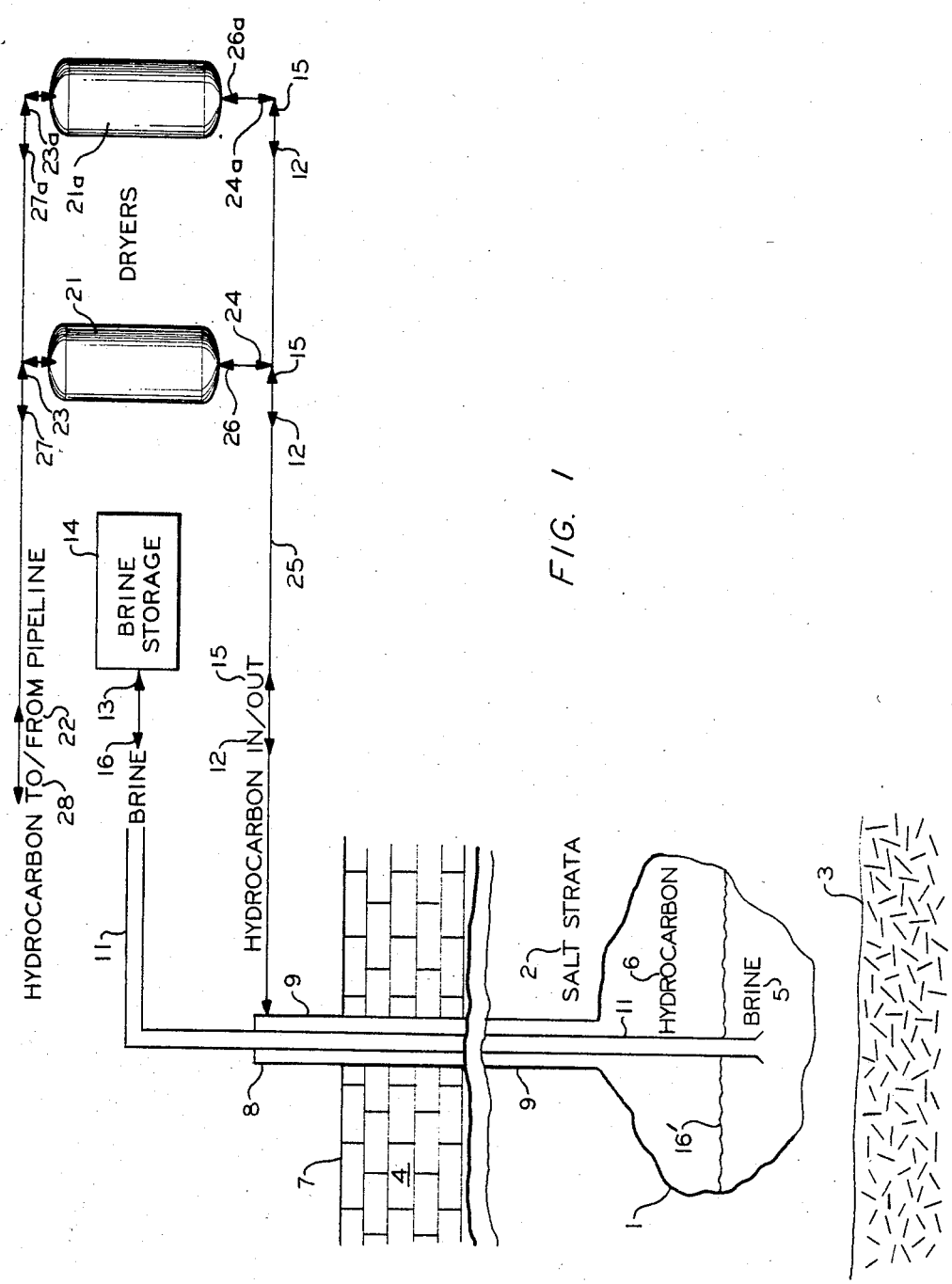

If supplementary drying for removal of any residual traces of moisture should be required for a particular end use, then conventional desiccation means can be employed with conventional heated gas regeneration of the desiccant. Such dehydration (desiccation) means are regenerated by temperature cycle employing a flow of heated gas, such as hot air, or combustion gases, or combination, to drive off absorbed moisture, followed by cool-down of the desiccant, and finally return to service. However, such operations are time-consuming, and energy-intensive. By my invention, the need for conventional drying means is greatly eliminated and in many instances can be eliminated. Clearly, the frequency between regenerations of the conventional units is greatly stretched out, saving time and fuel.

Hydrocarbon fluids delivered from the pipeline are received dry, are put through drier 21 or 21a, regenerate same by removing moisture therefrom, and then flow to storage. Hydrocarbon fluids in storage become moisture saturated, are withdrawn from storage, wet, the wet (moist) hydrocarbon fluids pass back through the driers, leave the moisture, and exit dry for return to the pipeline. Thus, hydrocarbon fluid to or from a salt storage cavern is passed via the same desiccant bed. Moisture removed from exiting hydrocarbon fluid to yield dry hydrocarbon fluid is in turn picked back up by dry hydrocarbon fluid entering the desiccant bed for storage in the cavern.

Storage caverns which are used in only one flow direction, that is, either in or out, need only one economizer drier bed, through more than one in sequence or tandem can be employed. Such bed or beds should be sized in accordance with maximum flow rates in or out. Dual beds, as shown in the drawing, can be employed, if desired, or other multiple beds depending on convenience for maintenance, need for alternation of flows, and the like.

Some storage caverns are used in an unusual fashion of both ingoing hydrocarbon fluid flow and outgoing hydrocarbon fluid flow at the same time, such as propylene storage. In this situation, for example, propylene being stored may be percolated through the brine for maximum residence time. Thus, propylene leaving the storage can be passed through a drier bed for drying to usage, while an alternate bed previously wetted by exiting propylene can be dried by dry propylene being piped into the cavern. When one bed becomes saturated and the other dry, then the flow through each can be rotated or alternated. For such operation a second conduit (not shown) between 1 and 21/21a will be required.

My cyclic process for regenerating saturated desiccant beds is effective, provides dry outflowing fluid, while drying and thus regenerating wetted desiccant beds as hydrocarbon fluid is returned or brought into the storage facility. If desired, conventional regeneration equipment could be used to augment the regeneration by incoming dry hydrocarbon.

HYDROCARBON FLUIDS

The hydrocarbon fluid can be normally liquid or gaseous, and under storage temperatures and pressures can be gaseous, compressed gaseous, or liquefied gaseous. The hydrocarbon can be saturated or unsaturated. For example, liquefied petroleum gas (LPG) is a frequently stored material. Liquefied propylene is a material frequently stored prior to use in polymerization or dimerization facilities.

DESICCANTS

Any of the normally solid desiccants which are not destroyed or changed in physical condition by moisture or hydrocarbon fluids or by exposure to traces of brines can be employed.

Among the suitable desiccants are such as calcium sulfate, silica gel, and preferably the molecular sieves, generally those of about 3 Å, 4 Å, or the like. Such molecular sieves and desiccants are well known in the art and require no particular further description. Suitable particle sizes are well known, and drier containers are well known in the art.

CALCULATED EXAMPLE

A typical operation can be illustrated further by means of a calculated operational example.

| Calculated Typical Operation | |
|---|---|
| Cycle I: | |
| Adding Dry Propylene Liquid to Salt Cavern: | |
| Dry Propylene To Wet Drier, barrels/hr. | 200 |
| Water Content (Dry), wt. % | nil |
| Pressure, psig | 600 |
| Temperature, °F. | 100 |
| Total Input (3 hrs.), barrels | 600 |
| Wet Propylene From Drier to Cavern, barrels/hr. | 200 |
| Water Content (wet), wt. % | 0.045 |
| Pressure, psig | 595 |
| Temperature, °F. | 100 |
| Total Output (3 hrs.), barrels | 600.14 |
| Water Removed From Drier, lbs. total | 49.4 |
| Brine (Saturated NaCl-water) out, barrels | 600.14 |
| Temperature, °F. | 100 |
| Cavern Conditions | |
| Pressure, avg., psig | 585 |
| Temperature, °F. | |
| Hydrocarbon | 100 |
| Brine | 100 |
| Cycle II: | |
| Removing Wet Propylene Liquid From Cavern: | |
| Wet Propylene Liquid to Dry Drier, barrels/hr. | 200 |
| Water Content (wet), wt. % | 0.055 |
| Pressure, psig | 550 |
| Temperature, °F. | 100 |
| Total Input (4 hrs.), barrels | 800.23 |
| Dry Propylene Liquid to Product, barrels/hr. | 200 |
| Water content (dry), wt. % | 0.010 |
| Pressure, psig | 545 |
| Temperature, °F. | 100 |
| Total Output (4 hrs.), barrels | 800.04 |
| Water Picked Up by Drier, lbs. total | 65.3 |
| Brine (Saturated NaCl-water) in, barrels | 800.23 |
| Temperature, °F. | 100 |

Reasonable variations and modifications of my invention are quite feasible, yet still within the scope of this disclosure and my claims without departing from the scope and spirit thereof.

I claim:

1. A hydrocarbon fluid storage system comprising in operable conjunction:
   a cavern formed within an underground salt strata below a ground surface, said cavern comprises a lower liquid volume of saturated sodium chloride storage brine and an upper fluid volume of wet hydrocarbon storage fluid,
   surface fluid handling means;
   conduit connecting said lower storage brine and upper storage hydrocarbon fluid with said surface fluid handling means, of fluid transfer means enabling transfer of brine and hydrocarbon fluid from said surface to said cavern and from said cavern to said surface, such that brine can be added to or withdrawn from said lower brine volume and hydrocarbon fluids can be added to or withdrawn from said upper hydrocarbon fluid volume, and at least one desiccant drier means positioned at the surface in operable association with said surface fluid handling means whereby said wet hydrocarbon fluid upon withdrawal from said cavern passes through said desiccant drier means and thereby becomes dry, and dry hydrocarbon fluid intended for storage passes through said desiccant drier prior to entering said storage cavern and thereby becomes wet.

2. The storage system according to claim 1 wherein said desiccant drier means comprises desiccant selected from the group consisting of molecular sieves, silica gel, and calcium sulfate.

3. The storage system according to claim 2 wherein said desiccant is a said molecular sieve and has a pore size of about 3 Å or 4 Å.

4. The storage system according to claim 3 wherein said hydrocarbon fluid is LPG.

5. The storage system according to claim 3 wherein said hydrocarbon fluid is propylene.

6. A hydrocarbon storage facility comprising in operable relationship:
a surface,
a cavity formed in an underground salt strata and having an upper volume and a lower volume,
connecting means between said surface and said upper volume suitable for fluid flow,
connecting means between said surface and said lower volume suitable for fluid flow,
a first fluid in said lower volume comprising salt brine,
a second fluid in some upper volume comprising a moisture wet hydrocarbon fluid,
first fluid transfer means positioned at the surface and adapted to withdraw said first fluid from said lower volume or replenish said first fluid in said lower volume,
first fluid transfer connecting means between said first fluid transfer means and said receiving means adapted
receiving means positioned at the surface and, adapted to receive dry second fluid,
second fluid transfer means adapted to withdraw said wet second fluid from said upper volume or replenish said wet second fluid in said upper volume,
dehydrating means at said surface,
second fluid transfer connecting means between said second fluid transfer means and said dehydrating means,
whereby said dry second fluid passes through said dehydrating means prior to passage to said upper volume, thereby becoming wet second fluid and returning moisture contained therein to said cavity, and whereby said wet second fluid passes through said dehydrating means upon withdrawal from said upper volume, thereby becoming dry second fluid.

7. The storage system according to claim 5 wherein said dehydrating means comprises a desiccant drier means containing desiccant selected from the group consisting of molecular sieves, silica gel, and calcium sulfate.

8. The storage system according to claim 7 wherein said desiccant is a said molecular sieve having a pore size of about 3 Å to 4 Å.

9. The storage system according to claim 8 wherein said hydrocarbon fluid is LPG.

10. The storage system according to claim 8 wherein said hydrocarbon fluid is propylene.

11. A method for moisturizing a relatively dry hydrocarbon fluid entering stream prior to storage in a salt cavern storage facility, which comprises:
(a) passing said relatively dry hydrocarbon fluid through at least one moisture wet desiccant bed, said relatively dry hydrocarbon fluid substantially stripping said moisture from said moisture wet desiccant bed thereby becoming an at least partically moisture wet hydrocarbon fluid and said moisture wet desiccant bed becoming a relatively dry desiccant bed,
passing said now at least partially moisture wet hydrocarbon fluid into said storage cavern;
thereafter, (b) withdrawing at least a portion of said moisture wet hydrocarbon fluid through said now dry desiccant bed, thereby becoming a dry exiting hydrocarbon fluid stream, and said desiccant bed becoming a moisture wet desiccant; and
(c) continuing alterating said steps (a) and (b).

12. The method according to claim 11 wherein said desiccant bed is selected from the group consisting of molecular sieves, silica gel and calcium sulfate.

13. The method according to claim 12 wherein said desiccant is said molecular sieves.

14. The method according to claim 13 wherein said hydrocarbon fluid is LPG.

15. The method according to claim 13 wherein said hydrocarbon fluid is propylene.

* * * * *

UNITED STATES PATENT AND TRADEMARK OFFICE
CERTIFICATE OF CORRECTION

PATENT NO. : 4,592,677
DATED : June 3, 1986
INVENTOR(S) : Stone P. Washer

It is certified that error appears in the above-identified patent and that said Letters Patent is hereby corrected as shown below:

Col. 6, line 12: delete "5" and substitute --- 6 --- therefor.

Col. 6, line 41: after "desiccant" insert --- bed ---.

Signed and Sealed this

Twenty-third Day of December, 1986

Attest:

DONALD J. QUIGG

Attesting Officer     Commissioner of Patents and Trademarks